United States Patent
Connolly (12)

(10) Patent No.: US 6,358,702 B1
(45) Date of Patent: Mar. 19, 2002

(54) POLYNUCLEOTIDES ENCODING HUMAN HOX C10

(75) Inventor: Timothy Connolly, Belmont, MA (US)

(73) Assignee: Osiris Therapeutics, Inc., Baltimore, MD (US)

( * ) Notice: Subject to any disclaimer, the term of this patent is extended or adjusted under 35 U.S.C. 154(b) by 0 days.

(21) Appl. No.: 09/165,827

(22) Filed: Oct. 2, 1998

Related U.S. Application Data

(60) Provisional application No. 60/060,998, filed on Oct. 3, 1997.

(51) Int. Cl.[7] .................... C12P 21/02; C12N 5/00; C12N 15/00; C07H 21/02; C07H 21/04
(52) U.S. Cl. ............... 435/69.1; 435/91.4; 435/320.1; 435/70.1; 435/325; 435/243; 536/23.1; 536/23.5
(58) Field of Search ................ 435/320.1, 325, 435/243, 69.1, 70.1, 91.4; 536/23.1, 23.5

(56) References Cited

PUBLICATIONS

Adams, M., et al., "Homo sapiens cDNA 5' end similar to homeobox Hox–C10," Database EMEST17, E.M.B.L. Databases, Accession Nos. AA314165 & AA307551 (Apr. 18, 1997).

Cannizaro, et al., "Human Homeo Box–containing Genes Located at Chromosome Regions 2q31—2q37 and 12q12—12q13," *Am J Hum Genet*, 41(1):1–15 (1987).

Flagiello, D., et al., "Distinct patterns of all–trans retinoic acid dependent expression of HOXB and HOXC homeogenes in human embryonal and small–cell lung carcinoma cell lines," *Febs Lett.*, 415:263–267 (1997).

Peterson, Ron L., "Isolation and Characterization of four Abdominal–B–Related Hox Genes Contained in the 5'Region of the murine Hoxc cluster," Citations from Dissertation Abstracts:DIS, 55–05B:1738–1878 (1994).

Pollack, et al., "Gain of function mutations for paralogous Hox genes: Implications for the evolution of Hox gene function," *Proc Natl Acad Sci USA*, 92:4492–4496 (1995).

Sharkey, M., et al., "Hox genes in evolution: protein surfaces and paralog groups," *Trends in Genetics*, 13(4):145–151 (1997).

*Primary Examiner*—David Guzo
*Assistant Examiner*—Gerald G. Leffers, Jr.
(74) *Attorney, Agent, or Firm*—Elliot M. Olstein; Alan J. Grant

(57) ABSTRACT

This invention relates to newly identified polynucleotides, polypeptides encoded by such polynucleotides, the use of such polynucleotides and polypeptides, as well as the production of such polynucleotides and polypeptides. More particularly, the polypeptides of the present invention are human Hox C10 polypeptides. The invention also relates to identifying mesenchymal stem cells (MSCs) or other cells comprising such polypeptides or polynucleotides that encode the polypeptides.

19 Claims, 5 Drawing Sheets

FIGURE 1A

```
TTG ACT CAC GCG CTG GCT GCG CTC TAG AAT AGT GGA TCC CCC GGG          45

CTG CAG GAT CGG CAC GAG CTC CGC TGT AGT ATT GCT CCT TAA AAA          90

CCC CTC TCT CTG AAA ATG ACA TGC CCT CGC AAT GTA ACT CCG AAC         135
                    Met Thr Cys Pro Arg Asn Val Thr Pro Asn
                                     5                        10

TCG TAC GCG GAG CCC TTG GCT GCG CCG GGA GGA GAT CGC TAT             180
Ser Tyr Ala Glu Pro Leu Ala Ala Pro Gly Gly Asp Arg Tyr
                 15                  20                  25

AAC CGG AAC GCA GGC ATG TAT ATG CAG TCT GGG AGT GAC TTC AAT         225
Asn Arg Asn Ala Gly Met Tyr Met Gln Ser Gly Ser Asp Phe Asn
             30                  35                      40

TGC GGG GTG ATG AAG GGC TGC GGG CTC GCG CCC TCG CTC TCC AAG         270
Cys Gly Val Met Lys Gly Cys Gly Leu Ala Pro Ser Leu Ser Lys
             45                  50                      55

AGG GAC GAG GGC AGC AGC CCC AGC CTC GCC CTC AAC ACC TAT CCG         315
Arg Asp Glu Gly Ser Ser Pro Ser Leu Ala Leu Asn Thr Tyr Pro
             60                  65                      70
```

FIGURE 1B

```
TCC TAC CTC TCG CAG CTG GAC TCC TGG GGC GAC CCC AAA GCC GCC    360
Ser Tyr Leu Ser Gln Leu Asp Ser Trp Gly Asp Pro Lys Ala Ala     85
            75              80

TAT CGC CTG GAA ACA ACT GTT GGC AAG CCG CTG TCC TCC TGC TCC    405
Tyr Arg Leu Glu Thr Thr Val Gly Lys Pro Leu Ser Ser Cys Ser    100
            90              95

TAC CCA CCT AGT GTC AAG GAG AAT GTC TGC TGC ATG TAC AGC TCC    450
Tyr Pro Pro Ser Val Lys Glu Asn Val Cys Cys Met Tyr Ser Ser    115
           105             110

GCA GAG AAG CGG GCG AAA AGT GGC CCC GAG GCA GCT CTC TAC TCC    495
Ala Glu Lys Arg Ala Lys Ser Gly Pro Glu Ala Ala Leu Tyr Ser    130
           120             125

CAC CCC TTG CCG GAG TCC TGC CTT GGG GAG CAC GAG GTA CCC GTG    540
His Pro Leu Pro Glu Ser Cys Leu Gly Glu His Glu Val Pro Val    145
           135             140

CCC AGC TAC TAC CGC GCC GCC AGC CCG AGC TAC TCC GCG CTG GAC AAG  585
Pro Ser Tyr Tyr Arg Ala Ser Pro Ser Tyr Ala Leu Asp Lys           160
           150             155
```

FIGURE 1C

```
ACG CCC CAC TGT TCT GGG GCC AAC GAC TTC GAA GCC CCT TTC GAG    630
Thr Pro His Cys Ser Gly Ala Asn Asp Phe Glu Ala Pro Phe Glu
            165                     170                 175

CAG CGG GCC AGT CTC AAC CCG CGC GCC GAA CAT CTG GAA TCG CCT    675
Gln Arg Ala Ser Leu Asn Pro Arg Ala Glu His Leu Glu Ser Pro
            180                     185                 190

CAG CTG GGG GGC AAA GTG AGT TTC CCT GAG ACC CCC AAG TCC GAC    720
Gln Leu Gly Gly Lys Val Ser Phe Pro Glu Thr Pro Lys Ser Asp
            195                     200                 205

AGC CAG ACC CCA GCC CCA ATG AAA TCA AGA CGG AAC AGA ACC TGG    765
Ser Gln Thr Pro Ala Pro Met Lys Ser Arg Arg Asn Arg Thr Trp
            210                     215                 220

CGG GCC CTA AAG GGA GCC CCT CGG AGA GCG AAA AGG AGA GGG CCC    810
Arg Ala Leu Lys Gly Ala Pro Arg Arg Ala Lys Arg Arg Gly Pro
            225                     230                 235

AAA GCT GCC GAT TCC AGC CCA GAC ACC TCG GAT AAC GAA GCG AAA    855
Lys Ala Ala Asp Ser Ser Pro Asp Thr Ser Asp Asn Glu Ala Lys
            240                     245                 250
```

FIGURE 1D

```
GAG GAG ATA AAG GCA GAA AAC ACC ACA GGA AAT TGG CTG ACA GCA        900
Glu Glu Ile Lys Ala Glu Asn Thr Thr Gly Asn Trp Leu Thr Ala
            255                 260                 265

AAG AGC GGA AGG AAG AGG TGC CCC TAT ACT AAA CAC CAG ACG            945
Lys Ser Gly Arg Lys Arg Cys Pro Tyr Thr Lys His Gln Thr
        270                 275                 280

CTG GAA TTG GAG TAA GAA TTC TGG TTC CAA TAT GAA TTG GAA GCG        990
Leu Glu Leu Glu

GGG AGC GCC GCC TGG AGA TTA GCA AGA CCA TTA ACC TTA CAG ACA       1035

GAC AAG TCA AAA TCT GGT TTC AAA ATC GCA GAA TGA AAC TCA AGA       1080

AAA TGA ACC GAG AGA ATC GGA TCC GGG AAC TGA CCT CCA ATT TTA       1125

ATT TCA CCT GAG AGC GCG GCT TTT CTT CCC TTC CCG TTC CCG TTC TTT   1170

CTT TTC CCC GCC CTT                                                1185
```

FIGURE 2

```
Clone 76     M T C P R N V T P N S Y A E P L A A
             | | | | | | | | | | | | | | | | |
Hox C10      M T C P R N V T P N S Y A E P L A A
(mouse)

Clone 76     P G G G D R Y N R N A G M Y M Q S G
             | | | |   | | | | | | | | | | | | |
Hox C10      P G G G E R Y N R N A G M Y M Q S G
(mouse)

Clone 76     S D F N C G V M K G C G L A P S P S
             | | | | | | | |   | | | | | |   |
Hox C10      S D F N C G V M R G C G L A P S L S
(mouse)

Clone 76     K R D E G S S L S L A L N T Y P
             | | | |   |     | | | | | | |
Hox C10      K R D E G G S P N L A L N T Y P
(mouse)
```

POLYNUCLEOTIDES ENCODING HUMAN HOX C10

This application claims priority of U.S. Provisional Application No. 60/060,998, filed Oct. 3, 1997.

This invention relates to newly identified polynucleotides, polypeptides encoded by such polynucleotides, the use of such polynucleotides and polypeptides, as well as the production of such polynucleotides and polypeptides. More particularly, the polypeptides of the present invention are human Hox C10 polypeptides. The invention also relates to identifying mesenchymal stem cells (MSCs) or other cells comprising such polypeptides or polynucleotides that encode the polypeptides.

The Hox family of transcription factors exhibit a wide variety of functions and may control the organization of the embryo along an anterior-posterior axis. Thus, the structure (e.g., limb) and organ (e.g., kidney) that develops in the embryo is strongly influenced by which Hox gene is expressed temporally and spatially in that region. In addition, Hox genes may play important lineage-specific roles in a number of mature tissues. The fact that the Hox genes determine pattern formation in embryos suggests that Hox genes perform important functions in pluripotent stem cell populations.

The expression of a Hox family gene, HoxB4, has been implicated as being important in controlling hematopoietic stem cell (HSC) proliferation.

Mesenchymal stem cells are the formative pluripotential cells found inter alia in bone marrow, blood, dermis and periosteum that are capable of differentiating into any of the specific types of mesenchymal or connective tissues (i.e. the tissues of the body that support the specialized elements; particularly adipose, osseous, cartilaginous, elastic, and fibrous connective tissues) depending upon various influences polypeptides growth from bioactive factors, such as polypeptide growth factors.

In accordance with one aspect of the present invention, there are provided novel polypeptides that are produced by MSCs as well as biologically active and diagnostically or therapeutically useful fragments, analogs and derivatives thereof.

In accordance with another aspect of the present invention, there are provided isolated nucleic acid molecules encoding such polypeptides, including precursor RNA, mRNAs, cDNAs, genomic DNA as well as biologically active and diagnostically or therapeutically useful fragments, analogs and derivatives thereof.

In accordance with another aspect of the present invention there is provided an isolated nucleic acid molecule encoding a mature polypeptide expressed by the DNA contained in material deposited with the ATCC on Oct. 2, 1997 and which has ATCC Deposit No. 209323.

In accordance with another aspect of the present invention there are provided nucleic acid probes comprising nucleic acid molecules of sufficient length to specifically hybridize to sequences of the present invention.

In accordance with yet a further aspect of the present invention, there is provided a process for producing such polypeptides by recombinant techniques which comprises culturing recombinant prokaryotic and/or eukaryotic host cells, containing a nucleic acid sequence of the present invention, under conditions promoting expression of said protein and subsequent recovery of said protein.

In accordance with yet a further aspect of the present invention, there is provided a process for utilizing such polypeptides, or polynucleotides encoding such polypeptides for identifying human MSCs by utilizing the polynucleotides as probes or by expressing the polypeptides encoded thereby, using such polypeptides to produce an antibody specific for one of the polypeptides and then utilizing the antibody to identify the MSCs. Further such polynucleotides, polypeptides and antibodies may be utilized to aid in the identification of MSCs from other species, as well as to investigate/identify MSC functions in humans or other species.

In accordance with yet a further aspect of the present invention, there are provided antibodies against such polypeptides and a method of employing such antibodies to detect diseases related to an overexpression or under expression of the polypeptide of the present invention.

In accordance with another aspect of the present invention there is provided a method of diagnosing a disease or a susceptibility to a disease related to a mutation in the nucleic acid sequences and the proteins encoded by such nucleic acid sequences.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A to 1D collectively, display the cDNA sequence of clone 76 (SEQ ID. NO:13) and corresponding deduced amino acid sequence of the human Hox C10 polypeptide of the present invention (SEQ ID NO:14). The standard three-letter abbreviations for amino acids are used. Sequencing was performed using a 377 Automated DNA sequencer (Perkin-Elmer/Applied Biosystems, Inc.).

FIG. 2 is an illustration of amino acid sequence homology between the N-terminal portions (first 70 amino acids) of the polypeptide of the present invention (SEQ ID NO:9) and the mouse Hox C10 protein (SEQ ID NO:10). Standard one-letter abbreviations for amino acids are used.

In accordance with an aspect of the present invention, there are provided isolated nucleic acids (polynucleotides) which encode the mature polypeptides having the deduced amino acid sequences of FIGS. 1A to 1D, collectively (SEQ ID NO:14). The mature forms with and without an N-terminal methionine group are contemplated.

Polynucleotides encoding the polypeptide of the present invention have been isolated from a human MSC cDNA library. The polypeptide contains an open reading frame encoding a protein of 284 amino acids. The protein exhibits a high degree of homology at the amino acid level to the N-terminal portion of mouse Hox C10 (first 70 amino acids) with 91.43% identity.

In accordance with another aspect of the present invention there are provided isolated polynucleotides encoding a mature polypeptide expressed by the DNA contained in ATCC Deposit No. 209323, deposited with the American Type Culture Collection, 10,801 University Boulevard, Manassas, Va. 20110, USA, on Oct. 2, 1997.

The deposit(s) have been made under the terms of the Budapest Treaty on the International Recognition of the Deposit of Micro-organisms for purposes of Patent Procedure. The strain will be irrevocably and without restriction or condition released to the public upon the issuance of a patent. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptides may be identical to the coding sequences shown collectively in FIGS. 1A to 1D (SEQ ID NO:13) or may be a different coding sequence which coding sequence, as a result of the redundancy or degeneracy of the genetic code, encodes the same mature polypeptides as the DNA collectively shown by FIGS. 1A to 1D (SEQ ID NO:13).

The polynucleotides which encode the mature polypeptides of FIGS. 1A to 1D (SEQ ID NO: 14) may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptides.

Thus, the term "polynucleotide encoding a polypeptide" encompasses a polynucleotide which includes coding sequence for the polypeptide and may also include additional coding and/or non-coding sequence such as introns.

The present invention further relates to variants of the hereinabove described polynucleotides which encode fragments, analogs and derivatives of the polypeptide having the deduced amino acid sequences as collectively shown in FIGS. 1A to 1D (SEQ ID NO: 14). The variant of the polynucleotides may be a naturally occurring allelic variant of the polynucleotides or a non-naturally occurring variant of the polynucleotides.

Further particularly preferred in this regard are polynucleotides encoding the human Hox C10 polypeptide variants, analogs, derivatives and fragments, and variants, analogs and derivatives of the fragments, which have the amino acid sequence of the polypeptide of FIGS. 1A to 1D or of the deposit in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the human Hox C10 protein. Also especially preferred in this regard are conservative substitutions. Most highly preferred are polypeptides having the amino acid sequence of collectively shown as FIGS. 1A to 1D or of the deposit, without substitutions.

Thus, the present invention includes polynucleotides encoding the same mature polypeptides as shown in FIGS. 1A to 1D(SEQ ID NO: 14) as well as variants of such polynucleotides which variants encode a fragment, derivative or analog of the polypeptides of FIGS. 1A to 1D (SEQ ID NO:14). Such nucleotide variants include deletion variants, substitution variants and addition or insertion variants.

As hereinabove indicated, the polynucleotides may have a coding sequence which is a naturally occurring allelic variant of the coding sequences shown in FIGS. 1A to 1D (SEQ ID NO: 13). As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptides may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotides of the present invention may encode a mature protein, or for a protein having a prosequence or for a protein having both a prosequence and a presequence (leader sequence). In such a host cell, an appropriate modification initiation mechanism is present to result in the mature protein or the mature protein may be obtained by modification after isolation from the host. Any modifications to protein may also be made after isolation.

The polynucleotides of the present invention may also have the coding sequence fused in frame to a marker sequence which allows for purification of the polypeptides of the present invention. The marker sequence may be a hexa-histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a fill length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNA of FIGS. 1A to 1D (SEQ ID NO: 14).

Alternatively, the polynucleotide may have at least 20 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:13, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:14 and polynucleotides complementary thereto as well as portions thereof, which portions have at least 20, preferably at least 30 consecutive bases and may have at least 50 consecutive bases and to polypeptides encoded by such polynucleotides.

The present invention further relates to polypeptides which have the deduced amino acid sequences of FIGS. 1A to 1D (SEQ ID NO: 14), as well as fragments, analogs and derivatives of such polypeptides.

The terms "fragment," "derivative" and "analog" when referring to the polypeptides of FIGS. 1A to 1D (SEQ ID NO: 14), means polypeptides which retain essentially the same biological function or activity as such polypeptides. Particularly preferred are $PO_4$ derivatives of the polypeptides. Thus, an analog includes a proprotein which can be activated by cleavage of the proprotein portion to produce an active mature polypeptide.

Among the particularly preferred embodiments of the invention in this regard are polypeptides having the amino acid sequence shown in FIGS. 1A to 1D, variants, analogs, derivatives and fragments thereof, and variants, analogs and derivatives of the fragments. Alternatively, particularly preferred embodiments of the invention in this regard are polypeptides having the amino acid sequence of the human chemotactic cytokine I of the cDNA in the deposited clone, variants, analogs, derivatives and fragments thereof, and variants, analogs and derivatives of the fragments.

Further particularly preferred in this regard are variants, analogs, derivatives and fragments, and variants, analogs and derivatives of the fragments, having the amino acid sequence of the polypeptide of FIGS. 1A to 1D or of the cDNA in the deposited clone, in which several, a few, 5 to 10, 1 to 5, 1 to 3, 2, 1 or no amino acid residues are substituted, deleted or added, in any combination. Especially preferred among these are silent substitutions, additions and deletions, which do not alter their properties and activities as compared to those of the human Hox C10 polypeptide. Also especially preferred in this regard are conservative substitutions. Most highly preferred are polypeptides having the amino acid sequence as shown in FIGS. 1A to 1D, or of the deposited clone, without substitutions.

The polypeptides of the present invention may be recombinant polypeptides, natural polypeptides or synthetic polypeptides, preferably recombinant polypeptides.

The fragment, derivative or analog of the polypeptides of FIGS. 1A to 1D (SEQ ID NO: 14) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO: 14 (in particular the mature polypeptide) as well as polypeptides which have at least 70% similarity (preferably at least 70% identity) to the polypeptide of SEQ ID NO:14, and which have at least 90% similarity (more preferably at least 90% identity) to the polypeptide of SEQ ID NO: 14 and still more preferably at least 95% similarity (still more preferably at least 95% identity) to the polypeptide of SEQ ID NO: 14 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include laci, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, lipofection, cationic liposomes or electroporation (Davis, L., Dibner, M., Battey, I., Basic Methods in Molecular Biology, (1986)).

The constructs in host cells can be used in a conventional manner to produce the gene products encoded by the recombinant sequences. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), and Common Protocols in Molecular Biology, Ausubel et al. (Eds.), John Wiley & Sons, New York (1987), the disclosures of which are hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa, 293 and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polynucleotides and polypeptides of the present invention may be employed as research reagents and materials for discovery of treatments and diagnostics for human disease. For example, the polynucleotides and polypeptides encoded by such polynucleotides can be utilized for in vitro purposes related to scientific research, synthesis of DNA and manufacture of DNA vectors and for designing therapeutics and diagnostics for the treatment of human disease.

The invention also provides a method for identifying human mesenchymal stem cells by contacting a mixture of mRNA from a cell sample with a polynucleotide unique to human Hox C10 and identifying any mRNA which has hybridized with the polynucleotide unique to human Hox C10. In a preferred embodiment the polynucleotide unique to human Hox C10 is bound to a solid support. Thus, for example, the identification of Hox C10 cDNA enables the Hox C10 nucleic acid sequence to be utilized as a diagnostic reagent to identify human MSCs, such as by using gene expression array technology. Labeled (e.g. fluorescent or radiolabeled) mixtures of total cellular mRNA hybridize to cognate elements of Hox C10 on a chip based array and allow for the accurate detection of genes specific to MSCs. This technology is described, for example, in Schena, Bioessays, 18(5):427–431 (May 1996) and O'Donnell-Maloney & Little, Genet. Anal., 13(6):151–157 (December 1996).

The polypeptides of the present invention and fragments and analogs and derivatives thereof may be identified by assays which detect MSC proliferation or other activity.

This invention is also related to the use of the human Hox C10 polypeptide gene as part of a diagnostic assay for detecting diseases or susceptibility to diseases related to the presence of mutations in the human Hox C10 polypeptide nucleic acid sequences. Such diseases are related to underexpression or overexpression of the human Hox C10 polypeptides.

Individuals carrying mutations in the human Hox C10 polypeptide gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding human Hox C10 polypeptide can be used to identify and analyze human Hox C10 polypeptide mutations. For example, deletions and insertions can be detected by a change in size of the amplified product in comparison to the normal genotype. Point mutations can be identified by hybridizing amplified DNA to radiolabeled human Hox C10 polypeptide RNA or alternatively, radiolabeled human Hox C10 polypeptide antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science*, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the Hox C10 polypeptide in various tissues since an over-expression or under-expression of the proteins compared to normal control tissue samples may detect the presence of a disease or susceptibility to a disease, for example, reduced blood cell counts or malignancies such as cancers and tumors. Assays used to detect levels of the Hox C10 polypeptide in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to the Hox C10 polypeptide antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any Hox C10 polypeptide attached to the polystyrene dish. All unbound monoclonal antibody is washed out with buffer. The reporter antibody linked to horseradish peroxidase is now placed in the dish resulting in binding of the reporter antibody to any monoclonal antibody bound to the Hox C10 polypeptide. Unattached reporter antibody is then washed out. Peroxidase substrates are then added to the dish and the amount of color developed in a given time period is a measurement of the amount of the Hox C10 polypeptide present in a given volume of patient sample when compared against a standard curve.

A competition assay may be employed wherein antibodies specific to the Hox C10 polypeptide are attached to a solid support and labeled the Hox C10 polypeptide and a sample derived from the host are passed over the solid support and the amount of label detected, for example by liquid scintillation chromatography, can be correlated to a quantity of the Hox C10 polypeptide in the sample.

A "sandwich" assay is similar to an ELISA assay. In a "sandwich" assay the Hox C10 polypeptide is passed over a solid support and binds to antibody attached to a solid support. A second antibody is then bound to the Hox C10 polypeptide. A third antibody which is labeled and specific to the second antibody is then passed over the solid support and binds to the second antibody and an amount can then be quantified.

This invention provides a method for identification of the receptors for the human the Hox C10 polypeptides. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to the polypeptides, and a cDNA library created from this RNA is divided into pools and used to transfect COS cells or other cells that are not responsive to the polypeptides. Transfected cells which are grown on glass slides are exposed to the labeled polypeptides. The polypeptides can be labeled by a variety of means including iodination or inclusion of a recognition site for the Hox C10 polypeptides. Following fixation and incubation, the slides are subjected to autoradiographic analysis. Positive pools are identified and sub-pools are prepared and retransfected using an iterative sub-pooling and rescreening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

This invention provides a method of screening compounds to identify agonists and antagonists to the human Hox C10 polypeptides of the present invention. An agonist is a compound which has similar biological functions of the polypeptides, while antagonists block such functions. Antagonists and agonists may be identified by the an MSC proliferation assay as is well known in the art.

Examples of potential the Hox C10 polypeptide antagonists include antibodies, or in some cases, oligonucleotides, which bind to the polypeptides. Another example of a potential antagonist is a negative dominant mutant of the polypeptides. Negative dominant mutants are polypeptides which bind to the receptor of the wild-type polypeptide, but fail to retain biological activity.

Antisense constructs prepared using antisense technology are also potential antagonists. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription (triple- helix, see Lee et al., Nucl. Acids Res., 6:3073 (1979); Cooney et al, Science, 241:456 (1988); and Dervan et al., Science, 251: 1360 (1991)), thereby preventing transcription and the production of the human Hox C10 polypeptide. The antisense RNA oligonucleotide hybridizes to the mRNA in vivo and blocks translation of the mRNA molecule into the polypeptides (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the human Hox C10 polypeptide.

Another potential human Hox C10 antagonist is a peptide derivative of the polypeptides which are naturally or synthetically modified analogs of the polypeptides that have lost biological function yet still recognize and bind to the receptors of the polypeptides to thereby effectively block the receptors. Examples of peptide derivatives include, but are not limited to, small peptides or peptide-like molecules.

Agonists to the Hox C10 polypeptide (determined to be agonists by a MSC proliferation assay, for example) may be employed to treat cases of bone marrow failure, for example, aplastic anemia and myelodysplastic syndrome or other proliferation related disorders.

The agonists or antagonists may be employed in a composition with a pharmaceutically acceptable carrier, e.g., as hereinafter described.

The human Hox C10 polypeptides and agonists and antagonists may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides and agonists and antagonists may be employed in conjunction with other therapeutic compounds.

The pharmaceutical compositions may be administered in a convenient manner such as by the topical, intravenous, intraperitoneal, intramuscular, intratumor, subcutaneous, intranasal or intradermal routes. The pharmaceutical compositions are administered in an amount which is effective for treating and/or prophylaxis of the specific indication. In general, the polypeptides will be administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The human Hox C10 polypeptides, and agonists or antagonists which are polypeptides, may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells. The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

Antibodies specific to the polypeptide of the present invention may be employed as a diagnostic to determine elevated or lowered levels of the polypeptide in a sample derived from a host by techniques known in the art. These elevated or lowered levels are indicative of certain disorders which are characterized by such levels of the protein of the present invention and members of its family.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

Such antibodies to the polypeptides of the present invention may be utilized to detect the presence or the absence of the polypeptides of the present invention. Thus, they are useful in an assay to verify the successful insertion of the polynucleotides of the present invention (as part of a construct) into a host cell. Thus, the protein encoded by the inserted polynucleotide according to the present invention, when expressed by the transformed host cell, serves as a "marker" for the successful insertion of the polynucleotide that can be detected by an antibody for the marker.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid OF DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

The present invention will be further described with reference to the following examples; however, it is to be understood that the present invention is not limited to such examples. All parts or amounts, unless otherwise specified, are by weight.

In order to facilitate understanding of the invention the following examples providing certain frequently occuring methods and/or terms will be described.

EXAMPLE 1

Bacterial Expression and Purification of Human Hox C10

The DNA sequence encoding for human Hox C10, ATCC # 209323, was amplified by PCR using the oligonucleotide primers corresponding to the 5' and 3' end sequences of the processed Hox C10 nucleic acid sequence.

The 5' primer has the sequence CGC GGA TCC TCT CTG AAA ATG ACA TGC C 3' (SEQ ID NO:11) and contains a Bam Hi restriction enzyme site (in bold) followed by 19 nucleotides of coding sequence.

The 3' primer has the sequence CGC GGA TCC CCA GAA TTC TTA CAC CAA T 3' (SEQ ID NO:12) and contains a Bam H1 restriction enzyme site (in bold) followed by 16 nucleotides complementary to the 3' untranslated sequence of the Hox C10 gene and stop codon.

The Hox C10 PCR fragment encoding full length Hox C10 polypeptide was ligated in frame into the pRSET (Invitrogen) bacterial expression vector. The pRSET vector contains 1) E. coli replication origin, 2) ampicillin resistance gene, 3) T7 promoter (M13 phage) followed by histidine residues and a polylinker region. The cDNA encoding the entire Hox C10 polypeptide is ligated into the polylinker region so that a recombinant Hox C10 protein is produced in bacteria and contain 6 histidine residues at the amino terminus of the mature Hox C10 polypeptide.

The Hox C10 polypeptide synthesis is induced in bacterial strains upon addition of T7 polymerase and/or IPTG in BL21 (Lys S) cells. The histidine tagged Hox C10 polypeptide is purified from bacterial cell lysates by gel chromatography using a nickel charged Probond Resin (Invitrogen). A bacterial cell containing histidine tagged Hox C10 polypeptide is lysed and a cell free lysate is prepared. The cell free lysate is incubated with a Probond Resin and non-specific cellular proteins are removed by washing the resin with neutral pH buffers. The recombinant Hox C10 polypeptide is eluted from the Probond Resin by incubation with low pH or imidazole containing buffers.

EXAMPLE 2

Expression of Recombinant Hox C10 in COS Cells

The DNA sequence encoding the full-length Hox C10, ATCC # 209323, is amplified using PCR oligonucleotide primers corresponding to the 5' and 3' sequences of the gene.

The 5' primer has the sequence CGC GGA TCC TCT CTG AAA ATG ACA TGC C 3' (SEQ ID NO:11) and contains a Bam H1 restriction enzyme site (in bold) followed by 19 nucleotides of coding sequence.

The 3' primer has the sequence CGC GGA TCC CCA GAA TTC TTA CAC CAA T 3' (SEQ ID NO:12) and contains a Bam H1 restriction enzyme site (in bold) followed by 16 nucleotides complementary to the 3' untranslated sequence of the Hox C10 gene and stop codon.

The expression of plasmid Hox C10-HA is derived from a vector pcDNA1.1 (Invitrogen) containing: 1) SV 40 origin of replication, 2) ampicillin resistance gene, 3) E. coli replication origin, 4) CMV promoter followed by a polylinker region, a SV 40 intron and polyadenylaton site. A DNA fragment encoding the entire Hox C10 polypeptide precursor and hemaglutinin (HA) tag is cloned into the polylinker region of the vector, therefore, the recombinant protein expression is directed under the CMV promoter.

The vector encoding the entire Hox C10 precursor is transfected into Cos cells by calcium phosphate or lipofection derived methods. Cells containing the Hox C10 expression construct are selected by resistance to G418 (neomycin). Cos cells expressing the Hox C10 polypeptide are detected by northern and immunoprecipitation/western blot analysis.

EXAMPLE 3

Expression of Hox C10 in the Baculovirus Expression System

The DNA sequence encoding the full-length Hox C10, ATCC # 209323, is amplified using PCR oligonucleotide primers corresponding to the 5' and 3' sequences of the gene.

The 5' primer has the sequence CGC GGA TCC TCT CTG AAA ATG ACA TGC C 3' (SEQ ID NO:11) and contains a Bam H1 restriction enzyme site (in bold) followed by 19 nucleotides of coding sequence.

The 3' primer has the sequence CGC GGA TCC CCA GAA TTC TTA CAC CAA T 3' (SEQ ID NO:12) and contains a Bam H1 restriction enzyme site (in bold) followed by 16 nucleotides complementary to the 3' sequence of the Hox C10 gene and stop codon.

The cDNA encoding the full-length Hox C10 polypeptide will be ligated into the pVL1392/1393 vectors (Pharmingen). The PVL1392/1393 vectors will contain the 1) *E. coli* replication origin, 2) ampicillin resistance gene, 3) polyhedrin promoter (*Autographa californica*) followed by a polylinker region. The recombinant protein will be produced in Sf9 cells from the polyhedrin promoter. The vector containing recombinant Hox C10 polypeptide will be transfected into Sf9 insect cells along with BaculoGold baculovirus DNA (Pharmingen). Sf9 cells, infected with baculovirus expressing Hox C10 full-length protein, will be harvested by gentle scraping and lysed in hypotonic buffer (30 mM KCI, 10 mM Hepes pH 6.8, 1 mM EDTA). The recombinant protein will be purified by conventional methods.

EXAMPLE 4

Gene Therapy by Expression of Hox C10 Gene Function

The DNA sequence encoding the full-length Hox C10, ATCC # 209323, is amplified using PCR oligonucleotide primers corresponding to the 5' and 3' sequences of the gene.

The 5' primer has the sequence CGC GGA TCC TCT CTG AAA ATG ACA TGC C 3' (SEQ ID NO:11) and contains a Bam H1 restriction enzyme site (in bold) followed by 19 nucleotides of coding sequence.

The 3' primer has the sequence CGC GGA TCC CCA GAA TTC TTA CAC CAA T 3' (SEQ ID NO:12) and contains a Bam H1 restriction enzyme site (in bold) followed by 16 nucleotides complementary to the 3' untranslated sequence of the Hox C10 gene and stop codon.

The Hox C10 cDNA sequence is cloned into a pVM5 retroviral vector which contains the neomycin phosphotransferase gene (neo) so that the Hox C10 cDNA is under the transcriptional control of the 5' long term repeat (LTR). Ecotropic viral supernatant is obtained by infection of E86 retroviral packaging cells with pVM5 Hox C10 construct. A clone transmitting a high viral titer is chosen for subsequent gene transfer procedures.

The construction of a retroviral vector expressing recombinant Hox C10 provides a useful tool to restore Hox C10 gene fimction in particular patients. Autologous human MSCs are obtained and culture expanded from particular patients as previously described (Haynesworth et al., 1992). Human MSCs are transfected with a retroviral suspension of pVM5 Hox C10. Individual clones of stable, retrovirally transduced human MSCs are selected by their resistance to G418 and for their expression of recombinant Hox C10 polypeptide. Autologous retrovirally transduced human MSCs are then infused into patients in order to restore Hox C10 gene function in the MSC cell population in vivo.

Numerous modifications and variations of the present invention are possible in light of the above teachings and, therefore, within the scope of the appended claims, the invention may be practiced otherwise than as particularly described.

---

What is claimed is:

1. An isolated polynucleotide comprising a member selected from the group consisting of:
   (a) a cDNA encoding a Hox C10 polypeptide and having at least 95% identity to a polynucleotide encoding a polypeptide comprising amino acids 2 to 284 of SEQ ID NO: 14, and
   (b) the complement of (a).

2. The isolated polynucleotide of claim 1 wherein the member is (a).

3. The isolated polynucleotide of claim 1 wherein said member is (a) and the polypeptide encoded by the cDNA of (a) comprises amino acids 1 to 284 of SEQ ID NO:14.

4. The isolated polynucleotide of claim 1 comprising a nucleotide sequence encoding a polypeptide comprising the amino acid sequence identical to amino acids 2 to 284 of SEQ ID NO:14.

5. The isolated polynucleotide of claim 1, wherein the polynucleotide is DNA.

6. The isolated polynucleotide of claim 1 comprising a nucleotide sequence encoding a polypeptide comprising the amino sequence identical to amino acids 1 to 284 of SEQ ID NO:14.

7. An isolated RNA encoding a Hox C10 polypeptide wherein said isolated RNA is encoded by the cDNA of claim 1.

8. A process of making a recombinant vector comprising inserting the polynucleotide of claim 2 into a vector, wherein said polynucleotide is DNA.

9. A recombinant vector comprising the polynucleotide of claim 2, wherein said polynucleotide is DNA.

10. A recombinant host cell comprising the polynucleotide of claim 2.

11. A process for producing a polypeptide comprising expressing from the recombinant cell of claim 10 the polypeptide encoded by said polynucleotide.

12. A process for producing a polypeptide comprising:
    expressing from a recombinant cell containing the polynucleotide of claim 4 the polypeptide encoded by said nucleotide sequence.

13. A process for producing a polypeptide comprising:
    expressing from a recombinant cell containing the polynucleotide of claim 6 the polypeptide encoded by said nucleotide.

14. The isolated polynucleotide of claim 1 comprising nucleotides 109 to 957 of SEQ ID NO:13.

15. The isolated polynucleotide of claim 1 comprising nucleotides 106 to 957 of SEQ ID NO:13.

16. The polynucleotide of claim 1 comprising the nucleotides of the sequence of SEQ ID NO:13.

17. An isolated polynucleotide comprising a polynucleotide having at least a 95% identity to a member selected from the group consisting of:
    (a) a polynucleotide encoding the same mature polypeptide encoded by the human cDNA in ATCC Deposit No. 209323; and
    (b) the complement of (a).

18. The isolated polynucleotide of claim 17, wherein the member is (a).

19. The isolated polynucleotide of claim 17, wherein said polynucleotide comprises DNA identical to the coding portion of the human cDNA in ATCC Deposit No. 209323 which encodes a mature polypeptide.

* * * * *

UNITED STATES PATENT AND TRADEMARK OFFICE
CERTIFICATE OF CORRECTION

PATENT NO.    : 6,358,702 B1
DATED         : March 19, 2002
INVENTOR(S)   : Timothy Connolly It is certified that error appears in the above-identified patent and that said Letters Patent is hereby corrected as shown below:

Column 4,
Line 61, please delete "fill" and insert therefor -- full --

Column 18,
Line 5, please delete "Bam Hi" insert therefor -- Bam H1 --

Signed and Sealed this

Fourth Day of March, 2003

JAMES E. ROGAN
*Director of the United States Patent and Trademark Office*

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
       (A) LENGTH: 1182 BASE PAIRS
       (B) TYPE: NUCLEIC ACID
       (C) STRANDEDNESS: SINGLE
       (D) TOPOLOGY: LINEAR (ii) MOLECULE TYPE: cDNA (xi) SEQUENCE DESCRIPTION: SEQ ID NO: 1:

```
TTG ACT CAC GCG CTG GCT GCG CTC TAG AAT AGT GGA TCC CCC GGG          45

CTG CAG GAT CGG CAC GAG CTC CGC TGT AGT ATT GCT CCT TAA AAA          90

CCC CTC TCT CTG AAA ATG ACA TGC CCT CGC AAT GTA ACT CCG AAC         135
                Met Thr Cys Pro Arg Asn Val Thr Pro Asn
                 5                                  10
```

```
TCG TAC GCG GAG CCC TTG GCT GCG CCG GGC GGA GGA GAT CGC TAT        180
Ser Tyr Ala Glu Pro Leu Ala Ala Pro Gly Gly Gly Asp Arg Tyr
                 15                  20                  25

AAC CGG AAC GCA GGC ATG TAT ATG CAG TCT GGG AGT GAC TTC AAT        225
Asn Arg Asn Ala Gly Met Tyr Met Gln Ser Gly Ser Asp Phe Asn
                 30                  35                  40

TGC GGG GTG ATG AAG GGC TGC GGG CTC GCG CCC TCG CTC TCC AAG        270
Cys Gly Val Met Lys Gly Cys Gly Leu Ala Pro Ser Leu Ser Lys
                 45                  50                  55

AGG GAC GAG GGC AGC AGC CCC AGC CTC GCC CTC AAC ACC TAT CCG        315
Arg Asp Glu Gly Ser Ser Pro Ser Leu Ala Leu Asn Thr Tyr Pro
                 60                  65                  70

TCC TAC CTC TCG CAG CTG GAC TCC TGG GGC GAC CCC AAA GCC GCC        360
Ser Tyr Leu Ser Gln Leu Asp Ser Trp Gly Asp Pro Lys Ala Ala
                 75                  80                  85

TAT CGC CTG GAA ACA ACT GTT GGC AAG CCG CTG TCC TCC TGC TCC        405
Tyr Arg Leu Glu Thr Thr Val Gly Arg Pro Leu Ser Ser Cys Ser
                 90                  95                 100

TAC CCA CCT AGT GTC AAG GAG GAG AAT GTC TGC TGC ATG TAC AGC        450
Tyr Pro Pro Ser Val Lys Glu Glu Asn Val Cys Cys Met Tyr Ser
                105                 110                 115

GCA GAG AAG CGG GCG AAA AGT GGC CCC GAG GCA GCT CTC TAC TCC        495
Ala Glu Lys Arg Ala Lys Ser Gly Pro Glu Ala Ala Leu Tyr Ser
                120                 125                 130

CAC CCC TTG CCG GAG TCC TGC CTT GGG GAG CAC GAG GTA CCC GTG        540
His Pro Leu Pro Glu Ser Cys Leu Gly Glu His Glu Val Pro Val
                135                 140                 145

CCC AGC TAC TAC CGC GCC AGC CCG AGC TAC TCC GCG CTG GAC AAG        585
Pro Ser Tyr Tyr Arg Ala Ser Pro Ser Tyr Ser Ala Leu Asp Lys
                150                 155                 160

ACG CCC CAC TGT TCT GGG GCC AAC GAC TTC GAA GCC CCT TTC GAG        630
Thr Pro His Cys Ser Gly Ala Asn Asp Phe Glu Ala Pro Phe Glu
                165                 170                 175

CAG CGG GCC AGT CTC AAC CCG CGC GCC GAA CAT CTG GAA TCG CCT        675
Gln Arg Ala Ser Leu Asn Pro Arg Ala Glu His Leu Glu Ser Pro
                180                 185                 190

CAG CTG GGG GGC AAA GTG AGT TTC CCT GAG ACC CCC AAG TCC GAC        720
Gln Leu Gly Gly Lys Val Ser Phe Pro Glu Thr Pro Lys Ser Asp
                195                 200                 205

AGC CAG ACC CCA GCC CCA ATG AAA TCA AGA CGG AAC AGA ACC TGG        765
Ser Gln Thr Pro Ala Pro Met Lys Ser Arg Arg Asn Arg Thr Trp
                210                 215                 220

CGG GCC CTA AAG GGA GCC CCT CGG AGA GCG AAA AGG AGA GGG CCC        810
Arg Ala Leu Lys Gly Ala Pro Arg Arg Ala Lys Arg Arg Gly Pro
                225                 230                 235

AAA GCT GCC GAT TCC AGC CCA GAC ACC TCG GAT AAC GAA GCG AAA        855
Lys Ala Ala Asp Ser Ser Pro Asp Thr Ser Asp Asn Glu Ala Lys
                240                 245                 250

GAG GAG ATA AAG GCA GAA AAC ACC ACA GGA AAT TGG CTG ACA GCA        900
Glu Glu Ile Lys Ala Glu Asn Thr Thr Gly Asn Trp Leu Thr Ala
                255                 260                 265

AAG AGC GGA AGG AAG AAG AGG TGC CCC TAT ACT AAA CAC CAG ACG        945
Lys Ser Gly Arg Lys Lys Arg Cys Pro Tyr Thr Lys His Gln Thr
                270                 275                 280

CTG GAA TTG GAG AAA GAA TTT CTG TTC AAT ATG TAT TTG ACG CGA        990
Leu Glu Leu Glu Lys Glu Phe Leu Phe Asn Met Tyr Leu Thr Arg
                285                 290                 295

GAG CGC CGC CTG GAG ATT AGC AAG ACC ATT AAC CTT ACA GAC AGA       1035
Glu Arg Arg Leu Glu Ile Ser Lys Thr Ile Asn Leu Thr Asp Arg
```

```
                           300                    305                    310
CAA GTC AAA ATC TGG TTT CAA AAT CGC AGA ATG AAA CTC AAG AAA              1080
Gln Val Lys Ile Trp Phe Gln Asn Arg Arg Met Lys Leu Lys Lys
                           315                    320                    325

ATG AAC CGA GAG AAT CGG ATC CGG GAA CTG ACC TCC AAT TTT AAT              1125
Met Asn Arg Glu Asn Arg Ile Arg Glu Leu Thr Ser Asn Phe Asn
                           330                    335                    340

TTC ACC TGA GAGCGCGGCT TTTCTTCTTC CCTTCCCGTT CTTTCTTTTC                   1174
Phe Thr

CCCGCCCT                                                                   1182

(2) INFORMATION FOR SEQ ID NO: 2:

(i) SEQUENCE CHARACTERISTICS:
        (A) LENGTH: 342 AMINO ACIDS
        (B) TYPE: AMINO ACID
        (C) STRANDEDNESS: <Unknown>
        (D) TOPOLOGY: LINEAR (ii) MOLECULE TYPE: PROTEIN (xi) SEQUENCE DESCRIPTION: SEQ ID NO: 2:

Met Thr Cys Pro Arg Asn Val Thr Pro Asn Ser Tyr Ala Glu Pro
                5                      10                      15

Leu Ala Ala Pro Gly Gly Gly Asp Arg Tyr Asn Arg Asn Ala Gly
                20                     25                      30

Met Tyr Met Gln Ser Gly Ser Asp Phe Asn Cys Gly Val Met Lys
                35                     40                      45

Gly Cys Gly Leu Ala Pro Ser Leu Ser Lys Arg Asp Glu Gly Ser
                50                     55                      60

Ser Pro Ser Leu Ala Leu Asn Thr Tyr Pro Ser Tyr Leu Ser Gln
                65                     70                      75

Leu Asp Ser Trp Gly Asp Pro Lys Ala Ala Tyr Arg Leu Glu Thr
                80                     85                      90

Thr Val Gly Arg Pro Leu Ser Ser Cys Ser Tyr Pro Pro Ser Val
                95                     100                     105

Lys Glu Glu Asn Val Cys Cys Met Tyr Ser Ala Glu Lys Arg Ala
                110                    115                     120

Lys Ser Gly Pro Glu Ala Ala Leu Tyr Ser His Pro Leu Pro Glu
                125                    130                     135

Ser Cys Leu Gly Glu His Glu Val Pro Val Pro Ser Tyr Tyr Arg
                140                    145                     150

Ala Ser Pro Ser Tyr Ser Ala Leu Asp Lys Thr Pro His Cys Ser
                155                    160                     165

Gly Ala Asn Asp Phe Glu Ala Pro Phe Glu Gln Arg Ala Ser Leu
                170                    175                     180

Asn Pro Arg Ala Glu His Leu Glu Ser Pro Gln Leu Gly Gly Lys
                185                    190                     195

Val Ser Phe Pro Glu Thr Pro Lys Ser Asp Ser Gln Thr Pro Ala
                200                    205                     210

Pro Met Lys Ser Arg Arg Asn Arg Thr Trp Arg Ala Leu Lys Gly
                215                    220                     225

Ala Pro Arg Arg Ala Lys Arg Arg Gly Pro Lys Ala Ala Asp Ser
                230                    235                     240

Ser Pro Asp Thr Ser Asp Asn Glu Ala Lys Glu Glu Ile Lys Ala
                245                    250                     255
```

```
Glu Asn Thr Thr Gly Asn Trp Leu Thr Ala Lys Ser Gly Arg Lys
                260                 265                 270

Lys Arg Cys Pro Tyr Thr Lys His Gln Thr Leu Glu Leu Glu Lys
                275                 280                 285

Glu Phe Leu Phe Asn Met Tyr Leu Thr Arg Glu Arg Leu Glu
                290                 295                 300

Ile Ser Lys Thr Ile Asn Leu Thr Asp Arg Gln Val Lys Ile Trp
                305                 310                 315

Phe Gln Asn Arg Arg Met Lys Leu Lys Lys Met Asn Arg Glu Asn
                320                 325                 330

Arg Ile Arg Glu Leu Thr Ser Asn Phe Asn Phe Thr
                335                 340
```

(2) INFORMATION FOR SEQ ID NO: 3:

(i) SEQUENCE CHARACTERISTICS:
        (A) LENGTH: 22 BASE PAIRS
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO: 3:

CGCGGATCCA TGACATGCCC TC                                      22

(2) INFORMATION FOR SEQ ID NO: 4:

(i) SEQUENCE CHARACTERISTICS:
        (A) LENGTH: 28 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO: 4:

CGCGGATCCC TACTCCAATT CCAGCGTC                          28

(2) INFORMATION FOR SEQ ID NO: 5:

(i) SEQUENCE CHARACTERISTICS:
        (A) LENGTH: 31 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO: 5:

GCGCGGATCC ACCATGACAT GCCCTCGCAA T                    31

(2) INFORMATION FOR SEQ ID NO: 6:

(i) SEQUENCE CHARACTERISTICS:
        (A) LENGTH: 55 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO: 6:

GCGCTCTAGA TCAAGCGTAG TCTGGGACGT CGTATGGGTA CTCCAATTCC AGCGT      55

(2) INFORMATION FOR SEQ ID NO: 7:

(i) SEQUENCE CHARACTERISTICS:
        (A) LENGTH: 29 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO: 7:

CGCGGATCCC ACATGCCCTC GCAATGTAA                                 29

(2) INFORMATION FOR SEQ ID NO: 8:

(i) SEQUENCE CHARACTERISTICS:
        (A) LENGTH: 28 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO: 8:

CGCGGATCCC TACTCCAATT CCAGCGTC                                  28

(2) INFORMATION FOR SEQ ID NO: 9

(i) SEQUENCE CHARACTERISTICS:
        (A) LENGTH: 70 AMINO ACIDS
        (B) TYPE: AMINO ACID
        (C) STRANDEDNESS: <Unknown>
        (D) TOPOLOGY: LINEAR (ii) MOLECULE TYPE: PEPTIDE (xi) SEQUENCE DESCRIPTION: SEQ ID NO: 9:

Met Thr Cys Pro Arg Asn Val Thr Pro Asn Ser Tyr Ala Glu Pro
             5                      10                   15

Leu Ala Ala Pro Gly Gly Gly Asp Arg Tyr Asn Arg Asn Ala Gly
            20                    25                   30

Met Tyr Met Gln Ser Gly Ser Asp Phe Asn Cys Gly Val Met Lys
            35                    40                   45

Gly Cys Gly Leu Ala Pro Ser Pro Ser Lys Arg Asp Glu Gly Ser
            50                    55                   60

Ser Leu Ser Leu Ala Leu Asn Thr Tyr Pro
            65                    70

(2) INFORMATION FOR SEQ ID NO: 10:

(i) SEQUENCE CHARACTERISTICS:
        (A) LENGTH: 70 AMINO ACIDS
        (B) TYPE: AMINO ACID
        (C) STRANDEDNESS: <Unknown>
        (D) TOPOLOGY: LINEAR (ii) MOLECULE TYPE: PEPTIDE (xi) SEQUENCE DESCRIPTION: SEQ ID NO: 10:

Met Thr Cys Pro Arg Asn Val Thr Pro Asn Ser Tyr Ala Glu Pro
             5                      10                   15

Leu Ala Ala Pro Gly Gly Gly Glu Arg Tyr Asn Arg Asn Ala Gly
            20                    25                   30

Met Tyr Met Gln Ser Gly Ser Asp Phe Asn Cys Gly Val Met Arg
            35                    40                   45

```
Gly Cys Gly Leu Ala Pro Ser Leu Ser Lys Arg Asp Glu Gly Gly
                50                  55                  60

Ser Pro Asn Leu Ala Leu Asn Thr Tyr Pro
                65                  70
```

(2) INFORMATION FOR SEQ ID NO: 11:

(i) SEQUENCE CHARACTERISTICS:
        (A) LENGTH: 28 BASES
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO: 11

```
CGCGGATCCT CTCTGAAAAT GACATGCC                              28
```

(2) INFORMATION FOR SEQ ID NO: 12:

(i) SEQUENCE CHARACTERISTICS:
        (A) LENGTH: 28 BASES
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO: 12

```
CGCGGATCCC CAGAATTCTT ACACCAAT                              28
```

(2) INFORMATION FOR SEQ ID NO: 13:

(i) SEQUENCE CHARACTERISTICS:
        (A) LENGTH: 1185 BASE PAIRS
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO: 13:

```
TTG ACT CAC GCG CTG GCT GCG CTC TAG AAT AGT GGA TCC CCC GGG    45

CTG CAG GAT CGG CAC GAG CTC CGC TGT AGT ATT GCT CCT TAA AAA    90

CCC CTC TCT CTG AAA ATG ACA TGC CCT CGC AAT GTA ACT CCG AAC   135

TCG TAC GCG GAG CCC TTG GCT GCG CCG GGC GGA GGA GAT CGC TAT   180

AAC CGG AAC GCA GGC ATG TAT ATG CAG TCT GGG AGT GAC TTC AAT   225

TGC GGG GTG ATG AAG GGC TGC GGG CTC GCG CCC TCG CTC TCC AAG   270

AGG GAC GAG GGC AGC AGC CCC AGC CTC GCC CTC AAC ACC TAT CCG   315

TCC TAC CTC TCG CAG CTG GAC TCC TGG GGC GAC CCC AAA GCC GCC   360

TAT CGC CTG GAA ACA ACT GTT GGC AAG CCG CTG TCC TCC TGC TCC   405

TAC CCA CCT AGT GTC AAG GAG GAG AAT GTC TGC TGC ATG TAC AGC   450

GCA GAG AAG CGG GCG AAA AGT GGC CCC GAG GCA GCT CTC TAC TCC   495

CAC CCC TTG CCG GAG TCC TGC CTT GGG GAG CAC GAG GTA CCC GTG   540

CCC AGC TAC TAC CGC GCC AGC CCG AGC TAC TCC GCG CTG GAC AAG   585

ACG CCC CAC TGT TCT GGG GCC AAC GAC TTC GAA GCC CCT TTC GAG   630

CAG CGG GCC AGT CTC AAC CCG CGC GCC GAA CAT CTG GAA TCG CCT   675
```

-continued

```
CAG CTG GGG GGC AAA GTG AGT TTC CCT GAG ACC CCC AAG TCC GAC        720

AGC CAG ACC CCA GCC CCA ATG AAA TCA AGA CGG AAC AGA ACC TGG        765

CGG GCC CTA AAG GGA GCC CCT CGG AGA GCG AAA AGG AGA GGG CCC        810

AAA GCT GCC GAT TCC AGC CCA GAC ACC TCG GAT AAC GAA GCG AAA        855

GAG GAG ATA AAG GCA GAA AAC ACC ACA GGA AAT TGG CTG ACA GCA        900

AAG AGC GGA AGG AAG AAG AGG TGC CCC TAT ACT AAA CAC CAG ACG        945

CTG GAA TTG GAG TAA GAA TTC TGG TTC CAA TAT GAA TTG GAA GCG        990

GGG AGC GCC GCC TGG AGA TTA GCA AGA CCA TTA ACC TTA CAG ACA       1035

GAC AAG TCA AAA TCT GGT TTC AAA ATC GCA GAA TGA AAC TCA AGA       1080

AAA TGA ACC GAG AGA ATC GGA TCC GGG AAC TGA CCT CCA ATT TTA       1125

ATT TCA CCT GAG AGC GCG GCT TTT CTT CTT CCC TTC CCG TTC TTT       1170

CTT TTC CCC GCC CTT                                                1185
```

(2) INFORMATION FOR SEQ ID NO: 14:

(i) SEQUENCE CHARACTERISTICS:
        (A) LENGTH: 284 AMINO ACIDS
        (B) TYPE: AMINO ACID
        (C) STRANDEDNESS: <Unknown>
        (D) TOPOLOGY: LINEAR (ii) MOLECULE TYPE: PROTEIN (xi) SEQUENCE DESCRIPTION: SEQ ID NO: 14:

```
Met Thr Cys Pro Arg Asn Val Thr Pro Asn Ser Tyr Ala Glu Pro
                  5                  10                  15

Leu Ala Ala Pro Gly Gly Asp Arg Tyr Asn Arg Asn Ala Gly
                 20                  25                  30

Met Tyr Met Gln Ser Gly Ser Asp Phe Asn Cys Gly Val Met Lys
                 35                  40                  45

Gly Cys Gly Leu Ala Pro Ser Leu Ser Lys Arg Asp Glu Gly Ser
                 50                  55                  60

Ser Pro Ser Leu Ala Leu Asn Thr Tyr Pro Ser Tyr Leu Ser Gln
                 65                  70                  75

Leu Asp Ser Trp Gly Asp Pro Lys Ala Ala Tyr Arg Leu Glu Thr
                 80                  85                  90

Thr Val Gly Arg Pro Leu Ser Ser Cys Ser Tyr Pro Pro Ser Val
                 95                 100                 105

Lys Glu Glu Asn Val Cys Cys Met Tyr Ser Ala Glu Lys Arg Ala
                110                 115                 120

Lys Ser Gly Pro Glu Ala Ala Leu Tyr Ser His Pro Leu Pro Glu
                125                 130                 135

Ser Cys Leu Gly Glu His Glu Val Pro Val Pro Ser Tyr Tyr Arg
                140                 145                 150

Ala Ser Pro Ser Tyr Ser Ala Leu Asp Lys Thr Pro His Cys Ser
                155                 160                 165

Gly Ala Asn Asp Phe Glu Ala Pro Phe Glu Gln Arg Ala Ser Leu
                170                 175                 180

Asn Pro Arg Ala Glu His Leu Glu Ser Pro Gln Leu Gly Gly Lys
                185                 190                 195

Val Ser Phe Pro Glu Thr Pro Lys Ser Asp Ser Gln Thr Pro Ala
                200                 205                 210
```

-continued

```
Pro Met Lys Ser Arg Arg Asn Arg Thr Trp Arg Ala Leu Lys Gly
                215                 220                 225

Ala Pro Arg Arg Ala Lys Arg Arg Gly Pro Lys Ala Ala Asp Ser
                230                 235                 240

Ser Pro Asp Thr Ser Asp Asn Glu Ala Lys Glu Ile Lys Ala
                245                 250                 255

Glu Asn Thr Thr Gly Asn Trp Leu Thr Ala Lys Ser Gly Arg Lys
                260                 265                 270

Lys Arg Cys Pro Tyr Thr Lys His Gln Thr Leu Glu Leu Glu
                275                 280
```